United States Patent [19]

Kurane et al.

[11] 4,332,904
[45] * Jun. 1, 1982

[54] BIOCHEMICAL TREATMENT BY MICROORGANIC METHOD

[75] Inventors: Ryuichiro Kurane; Tomoo Suzuki; Yoshimasa Takahara, all of Chiba, Japan

[73] Assignee: Agency of Industrial Science & Technology, Ministry of International Trade & Industry, Tokyo, Japan

[*] Notice: The portion of the term of this patent subsequent to Jan. 9, 1996, has been disclaimed.

[21] Appl. No.: 30,766

[22] Filed: Apr. 17, 1979

Related U.S. Application Data

[63] Continuation-in-part of Ser. No. 863,046, Dec. 21, 1977, abandoned.

[30] Foreign Application Priority Data

Dec. 25, 1976 [JP] Japan ................................ 51/157017

[51] Int. Cl.$^3$ .......................... C12N 1/20; C12P 7/50; C02F 3/00
[52] U.S. Cl. ..................................... 435/262; 435/142; 435/155; 435/176; 435/253; 435/813; 210/611; 210/617; 210/618
[58] Field of Search ............... 435/253, 262, 176, 177, 435/174, 813, 245, 142, 155; 210/2, 11, 601, 615, 616, 617, 618, 610, 611

[56] References Cited

U.S. PATENT DOCUMENTS

| | | | |
|---|---|---|---|
| 1,991,993 | 2/1935 | Werkman et al. | 435/141 |
| 2,793,096 | 5/1957 | Pomeroy | 435/266 |
| 3,940,332 | 2/1976 | Kato et al. | 210/2 |
| 3,979,283 | 9/1976 | Prudom | 435/262 |
| 4,032,407 | 6/1977 | Scott et al. | 435/177 |
| 4,127,447 | 11/1978 | Griffith et al. | 435/813 |
| 4,133,752 | 1/1979 | Kurane et al. | 210/2 |

Primary Examiner—Thomas G. Wiseman
Attorney, Agent, or Firm—Oblon, Fisher, Spivak, McClelland & Maier

[57] ABSTRACT

A vessel capable of passing a liquid therethrough is packed with a support having at least hydrophilicity and microorganism cells are inoculated to the support, retained and cultivated therein. A reaction substrate is fed to the vessel and brought into contact with the microorganism, whereby the microorganism is allowed to propagate within the support and act upon the reaction substrate to induce decomposition or synthetic reactions thereof.

3 Claims, No Drawings

BIOCHEMICAL TREATMENT BY MICROORGANIC METHOD

REFERENCE TO RELATED APPLICATION

This is a continuation-in-part application of our co-pending application U.S. Ser. No. 863,046 filed Dec. 21, 1977 now abandoned.

BACKGROUND OF THE INVENTION

This invention relates to improvements in and concerning a method for fixing microorganisms. More particularly, the present invention relates to a microorganism method of reaction for the decomposition or synthesis of a reaction substrate, which method is characterized by utilizing conditions for permitting a microorganism to be positively retained and grown on a support in the cultivation of the microorganism and by causing the reaction substrate to come into contact with the support on which the microorganism has been retained.

In recent years, microorganisms have been finding extensive utility in disposal of effluents responsible for environmental pollution, production of foodstuffs, manufacture of pharmaceutical goods, etc.

In one area of the utility, microorganisms are used for producing enzymes, which are adopted to effect various biochemical reactions leading to production of useful substances. Such enzymatic reactions were formerly carried out by a batchwise method wherein either the enzymes themselves or microorganism cells containing such enzymes were incorporated in reaction substrates. Ther have since been developed methods for fixing enzymes in proper carriers or for fixing enzymes in the microorganism cells in which they are produced (for example, these methods disclosed in U.S. Pat. Nos. 3,752,858, 3,933,587 and 3,950,222), making it feasible for desired enzymatic reactions to be continuously carried out. These methods have invariably had a fatal disadvantage in that the microorganism cells which have produced the enzymes are no longer allowed to propagate because the cells are dead at the time the enzymes are fixed therein or because the enzymes are extracted from the cells prior to the fixation in the carriers and that, consequently, the activities of the fixed enzymes inevitably gradually decrease with the progress of the enzymatic reactions involved.

The inventors have suggested a method for the decomposition of phthalic acid esters by use of a microorganism (U.S. Pat. No. 4,133,752). This method comprises incorporating a phthalic acid ester in a culture medium and culturing a specific microorganism in said medium for thereby causing the microorganism to propagate and assimilate the phthalic acid ester to effect the required decomposition. By this method, however, it has been difficult to effect the decomposition of the phthalic acid ester in a continuous process.

Besides, U.S. Pat. No. 2,793,096 discloses a method for de-odorizing an odorous gas by forcing the gas to flow into a gas-permeable soil bed inhabited by a microorganism and thereby causing the odors present in the gas to be oxidized by the microorganism. This method, however, makes use of the microorganism existing from the beginning in the soil bed and the substance to be treated thereby is a gaseous matter. That is to say, the reaction efficiency of this method depends completely upon a microorganism which might by chance exist in the soil bed. When the soil bed to be used contains therein no microorganism capable of oxidizing and de-odorizing odorous substances, it is self-evident that good results cannot be expected by this method.

An object of the present invention is to provide a microorganism method for enabling a biochemical treatment for decomposition or synthesis to be performed continuously and effectively by the agency of a microorganism for a long period of time.

SUMMARY OF THE INVENTION

To accomplish the object described above, the present invention provides a method of biochemical reaction which comprises packing a vessel capable of passing liquids therethrough with a support comprising soil possessing at least hydrophilicity and having a pH value in the range of from 3 to 9, inoculating said soil support with a microorganism, passing an aqueous dispersion of a reaction substrate through the vessel thereby permitting said microorganism to contact and react with the reaction substrate, and maintaining the growth of the microorganism while the microorganism continues to react with the passing reaction substrate.

Since the microorganism, according to the method of this invention, is retained alive and active in the support and thus is kept available continuously for contact with the reaction substrate, it grows and gains in activity so as to act stably upon the reaction substrate which is continuously brought into contact therewith over a long period of time.

The reaction substrate can also be treated by inoculating to the support activated sludge in place of the microorganism. In this case, more effective treatment of the reaction substrate can be accomplished by acclimatizing prior to the inoculation the activated sludge with the reaction substrate for thereby propagating the microorganism assimilating the reaction substrate in the activated sludge.

When a vessel capable of passing a liquid therethrough is packed with the support having the microorganism retained alive and active therein, the reaction of the reaction substrate can be continuously obtained by simple passing the reaction substrate through the vessel. Since the present invention causes the microorganism to be retained alive and active in the support and to be used in the reaction, it can also be used for enzyme reactions involving the enzyme to be produced by the retained microorganism and it further permits the disposal of ecologically waste water harmful effluents, the manufacture of pharmaceutical goods and the production of foodstuffs to be effectively and economically carried out by the action of the retained microorganism.

The other objects and characteristic features of the present invention will become apparent from the description of the invention to be given in detail hereinafter.

DESCRIPTION OF THE PREFERRED EMBODIMENT

In a reaction using a microorganism, even if the microorganism is fixed in a suitable support, there nevertheless ensures a problem that the activity of the fixed microorganism is gradually degraded with the progress of the reaction and, for that reason, the continued reaction aimed at by the use of the fixed microorganism is difficult to attain. With a view to finding a perfect solution to this problem, the inventors continued a series of studies in search of a method whereby the microorganism is retained alive and active in a support and the reaction substrate is continuously brought into contact with the retained microorganism so as to enable the microorganism to grow within the support, maintain the activity constantly and act stably upon the reaction substrate to provide a continued reaction. They have, consequently, perfected the present invention.

To be specific, the present invention effects the decomposition or synthetic reactions of a given reaction substrate continuously by causing at least one microorganism to be inoculated to, retained and cultivated in a suitable hydrophilic support, packing a vessel of a construction capable of passing a liquid therethrough with the support, feeding the reaction substrate to the vessel and bringing it into contact with the microorganism retained in the support. Of course, the same effect can be obtained by first packing the vessel with the support, then inoculating the microorganism to the support, causing the inoculated microorganism to be retained and cultivated within the support and bringing the reaction substrate into contact with the retained microorganism.

Because of the requirement that the microorganism inoculated to the support should be retained and cultivated therein, the support to be used in the present invention must be a hydrophilic substance. This support, however, is required to remain stationary within the vessel capable of passing a liquid therethrough and permit passage of the reaction substrate therethrough for contact with the retained microorganism. When the substance selected as the support is deficient in permeability to water, it is desirable that it have its water-permeability properly improved by incorporation of a suitable amount of a hydrophobic substance. As an ideal substance which combines hydrophilicity with hydrophobicity and permits the microorganism to be retained and cultivated advantageously therein, there can be cited soil. Of the various kinds of soil available, preferably are humus soil and clayish loam which are composed of coarse grains. And, synthetic soils and soil conditioners available in the market are also usable.

Examples of substances abounding with hydrophilicity include activated carbon, zeolite, powdered particles of biscuit ware, rice hulls and cotton waste. Examples of suitable hydrophobic substances are sea sand, pulverized plastic particles, granular concrete particles, etc.

It will be understood from the foregoing description that any substance can be used only if it permits the microorganism to be retained and cultivated therein and that the substance may suitably be mixed with a hydrophobic substance where the inherent water-permeability thereof is insufficient and must be enhanced. The support, therefore, can be formed by using one member or a mixture of two or more members suitably selected from those substances mentioned above, with due consideration to the kind of microorganism to be used, the structure of the reaction vessel, the reaction conditions involved, etc. Examples of reaction vessels structurally capable of stationarily holding the support therein and passing a liquid therethrough include ordinary columns, horizontal reaction tanks, packed columns and vessels of other similar designs. In fact, any vessel can be used so long as it stationarily holds the support of the aforementioned description therein and permits flow of a liquid therethrough. The shape and dimensions of the vessel to be used may suitably be selected by taking into due consideration the kind of amount of the reaction substrate to be passed, the conditions of the treatment of the reaction substrate, the particular position at which the vessel is to be installed, and other similar factors.

As concerns the inoculation of the microorganism to the support, it is generally desirable to have the microorganism precultured or tamed in the presence of a reaction substrate to be subjected to the treatment and inoculate the support with the microorganism resulting from the preculture or acclimatization. The inoculation of the microorganism may be carried out either before the support is placed in the reaction vessel or after it has been placed in the vessel. To ensure advantageous retention of the microorganism within the support, however, it is desirable for the pH value of the support to fall in the range of from 3 to 9, preferably from 5 to 8, without reference to the pH value appropriate for the growth of the microorganism or to the kind of the support itself. Where a substance such as humus soil which from the beginning has some source of nourishment is used as the support, there is no particular need for adding to the substance any nourishing source. Where there is used a substance which is devoid of a nutritional component or which is deficient in nutritional value, it becomes necessary to provide the substance with a nutritional source suitable for the particular microorganism to be inoculated to the support. As such a nutritional source, that which is used in the solution culture of the microorganism is added. The incorporation of the nutritional source to the support may be accomplished either by feeding the source directly to the vessel which has already been packed with the support or by adding the source to the support before the vessel is packed with that support. in the case of a reaction which is to be effected by the enzyme produced by the microorganism, the support is to be given an inducer for the formation of enzyme.

With lapse of time, the microorganism thus inoculated to the support is retained and cultivated on the surface of the support particles, in the inter-particle spaces of the support, in the cavities formed within the support particles, etc. After the microorganism has been retained and cultivated in the support and has propagated to the extent of acquiring a prescribed degree of activity, the feeding of the reaction substrate to the vessel is started to expose the retained microorganism to contact with the substrate. Since the contact of the reaction substrate with the microorganism is effected by passing the reaction substrate in the form of an aqueous solution through the vessel, the reaction substrate is desired to be available originally in a liquid form or powdered form. Desirably, the reaction substrate will be dissolved in or mixed with an aqueous solution so as to maximize its interface of contact with the retained microorganism. Where the reaction substrate happens to be in a solid form, it may be caused to undergo a synthetic or decomposition reaction with the retained microorganism though at a gradual rate of speed when the solid reaction substrate is placed on top of the support inside the vessel and an aqueous solution is made to flow through and dissolve the layer of the substrate.

No special limitation is imposed on the kind of the reaction substrate to be used for the treatment so long as it enables the microorganism to cause a synthetic or decomposition reaction of the substrate. Examples of reaction substrates advantageously used include organic carbohydrates, hydrocarbons, organic decays, night soil, starch, glucose, waste water containing petroleum or proteins and other substances bearing upon food products.

Therefore, the microorganism with which the present invention can be put to use include those capable of decomposing substances difficult to decompose such as, for example, phthalate-decomposing microorganisms and polyvinyl alcohol-decomposing microorganisms and those usable for the production of foodstuffs such as, for example, melibiase-producing microorganisms, glucose-isomerase-producing microorganisms and amylase-producing microorganisms. Such microorganisms can be used not merely in pure forms but also in complex forms or even in the form of colonies.

Generally the reaction of such a microorganism with the given reaction substrate proceeds with improved efficiency when the microorganism is pre-cultivated or acclimated with the reaction substrate in advance to the inoculation of the microorganism to the support. Particularly when the reaction involves use of activated sludge, about one week's acclimation of the activated sludge with the given reaction substrate results in a notable change in the microflora of the activated sludge such that the population of microorganisms capable of assimilating the reaction substrate is increased to improve notably the results of the reaction. When the activated sludge is acclimated, for example, with a protein-containing waste water for one week and then examined for microflora, it is ascertained that the proportion of Pseudomonas microorganisms to all the microorganisms present is increased to about 10% from the normally expected level of 1 to 2%.

Generally, the treatment of waste water with activated sludge, when the concentration of the waste water is high, gives rise to bulking and deflocculation phenomena which prevents spontaneous precipitation of the activated sludge. However, since the present invention effects mixing activated sludge with a support (soil), packing a vessel with the resultant mixture and supplying waste water into the vessel, it is unnecessary to give consideration to bulking and deflocculation phenomena and, therefore, even high-concentration waste water can be treated according to the present invention.

The amount of the microorganism or activated sludge to be inoculated to the support is not specified because the microorganism is suddenly propagated by bringing the microorganism into contact with the reaction substrate and maintaining the microorganism under conditions suitable for the cultivation even when the initial activity of the microorganism is low due to a small amount of the inoculated microorganism.

Now the method of this invention will be described more specifically hereinafter.

When soil is selected for use as the support, it is first dried in a stream of air, pulverized finely and passed through a sieve to remove excessively fine soil particles and large lumps of soil and collect soil particles having diameters in the approximate range of from 0.1 to 1.0 mm. When sawdust is selected as the support, it is mixed with a hydrophobic substance such as sea sand so as to be improved in water-permeability. When the vessel in which the mixture is placed happens to be a vertical column, this mixture may be homogeneous throughout the entire height of the column interior or the ratio of sea sand to sawdust in the mixture may be increased in the descending direction of the column. The possibility of the aqueous solution stagnating on the upper surface of the suport in the vessel can be precluded by incorporating the hydrophobic substance in an increased ratio in the upper portion of the support. The manner and proportion of the incorporation of such a hydrophobic substance are suitably selected with due consideration to the particular kind of the hydrophobic substance used, the kind of the microorganism inoculated to the support, the kind of reaction substrate, the shape of the vessel, the reaction conditions involved and other similar factors.

As regards the inoculation of the microorganism to the support, the cells of the microorganism may be uniformly mixed with the support or they may be inoculated concentrically to the portion of the support located in the neighborhood of the entrance to the vessel where the substrate is constantly exposed to contact with fresh supply of the reaction substrate. Although the microorganism cells at the time of the inoculation are desired to be alive and in the phase of logarithmic growth, those in the resting state may effectively used insofar as they are not dead.

The pH status of the support in connection with the inoculation of the microorganism was studied by using *Nocardia erythropolis* KR-S-1 (FERM P-No. 3530) for example. Specimens of a soil adjusted to varying pH values of from 2 to 10 as indicated in the table below and sea sand were mixed in a fixed voluminal ratio of 1:2 to produce different support specimens. A 1 g portion of each support specimen was thoroughly blended with 0.5 ml of germfree water having the *Nocardia erythropolis* suspended therein. The mixture was left to stand at rest for 10 minutes and the sample thus prepared was thoroughly mixed with 2 ml of germfree water and then left to stand at rest for 30 minutes. The supernatant formed on the sample was tested for absorbancy (O.D. 660) as the criterion for the ratio of microorganism cells suspended in the supernatant. The results of this test were as shown in Table 1 below.

TABLE 1

| pH | 2 | 3 | 4 | 5 | 6 | 7 | 8 | 9 | 10 |
|---|---|---|---|---|---|---|---|---|---|
| Absorbancy | 0.10 | 0.05 | 0.01 | 0.01 | 0.01 | 0.01 | 0.01 | 0.04 | 0.10 |

From this table, it is seen that the values of absorbancy were low in the supernatants from the samples having pH values (4 to 8) in the neutral zone. In consideration of the fact that the ratio of microorganism cells suspended in the supernatant decreases and the value of absorbancy is consequently lowered in proportion as the effectiveness of the retention of the cells within the support increases and, conversely, the ratio of microorganism cells suspended remains unchanged and the value of absorbancy is consequently elevated in proportion as the effectiveness decreases. Thus, the low values of absorbancy in the samples of neutral pH values suggest that the microorganism cells in these samples were substantially wholly retained within the supports.

The foregoing data definitely indicate that, in the case of *Nocardia erythropolis*, the retention of the microorganism cells in the support is advantageously effected when the support is adjusted to pH 4–8. They would also seem to warrant the conclusion that, even in the case of other microorganisms, the retention of the cells in the support is obtained advantageously by adjusting the pH value of the support to the range of from 4 to 8 without reference to the particular pH level optimal for the growth of the particular microorganism in use.

When the microorganism thus inoculated to the support has not yet been activated to the minimum level necessary for the purpose of the reaction involved or when the microorganism is in the resting state at the time of inoculation, the support in the vessel must be maintained under conditions desirable for the growth of the microorganism and, when necessary, a nutritional source or an inducer may be incorporated into the support. Generally, the reaction of the microorganism with the reaction substrate is improved when the microorganism is pre-cultivated or acclimated with the reaction substrate in advance to the inoculation of the microorganism to the support. After the microorganism in the support has been activated to the stated level, the substance subjected to the treatment (reaction substrate) is fed to the vessel and brought into contact with the retained microorganism. Generally, this contact of the reaction substrate with the retained microorganism is effected by having the substrate dissolved in water or a solvent and passing the resultant solution through the vessel. The reaction substrate is not necessarily required to be soluble in water. In the case of an oily reaction substrate such as, for example, a phthalic acid ester, it may be dispersed in a solvent with the aid of a surfactant so as to increase the interface of contact with the microorganism as much as possible. When the reaction substrate is in a fibrous form or a powdered form, it may be placed on the support held stationarily within the vessel and a suitable solvent passed through the vessel so that the substrate will be gradually dissolved away and allowed to flow through the support successively.

In order for the reaction of the microorganism with the reaction substrate to proceed effectively, when the microorganism is aerobic, it is desirable that the aqueous solution being passed through the vessel be suitably treated such as by aeration. To improve the permeability of the support to air and water, a hydrophobic substance such as sea and is added amply to the support. The temperature and pH value of the reaction system may be freely selected in ranges within which the microorganism attains growth. For the retention and propagation of the microorganism in the support, it is advantageous to add a necessary nutritional source to the aqueous solution which is being supplied to the support. Examples of nutritional sources which are favorable for the purpose include carbon sources, inorganic salts, inorganic nitrogen sources, organic nitrogen sources, vitamines, night soil, animal dung, wastes from agricultural produces, wastes from food industries, spent fermentation broths and residues, city garbage, etc. The kind and amount of the nutritional source are selected in accordance with the particular kind of microorganism inoculated or the conditions of the reaction.

When the solution of the reaction substrate is fed to the vessel as described above, it penetrates through the fine gaps formed inside the support and comes into contact with the retained microoganism, with the result that the reaction substrate in the solution is assimilated by the microorganism. The microorganism assimilates the reaction substrate and consumes the nutritional source, attains propagation steadily while being retained with increasing fastness within the support. In this manner, the reaction effectively proceeds.

The vessel in which the support having the microorganism retained and cultivated therein is stationarily held in position may have any shape which permits passage of the solution of reaction substrate. When the vessel is in the shape of a column, it is desirable to have the solution of reaction substrate downwardly fed thereto. And the downward feeding is desired to be effected by virture of gravitation, although it may otherwise been accomplished by means of suction or pressure. The shape and dimensions of the vessel are suitably selected with due consideration to the kind and amount of support, the kind of microorganism, the amount of the microorganism inoculated, the kind of the reaction substrate, the amount of the reaction substrate involved in the reaction, the reaction conditions, etc. Where the nature of the reaction is such that it consumes much time, for example, sufficient reaction time can be given by increasing the length of the column or the reaction time can be shortened by heightening the activity of the microorganism. In the case of a reaction which proceeds quickly, the support may be diluted with a large amount of hydrophobic substance or the feed rate of the solution of reaction substrate to the vessel may be increased.

Unlike any of the conventional methods suggested for the fixation of microorganisms, the present invention causes the microorganism to be retained alive and active in the support, held in that state to be contacted by the reaction substrate, causing a synthetic or decomposition reaction of the reaction substrate as clearly described above. When the retained microorganism is continually replenished with its nutritional source and is consequently allowed to remain active continuously, the desired microorganic reaction can be obtained continuously and stably over a prolonged period of time.

Since this invention is applicable to virtually every microorganism, the range of reaction substrates on which the invention is effectively worked is very wide. Thus, the invention can be applied to various reactions ranging from the disposal of ecologically harmful effluents to the production of foodstuffs. As the support for the microorganism, various naturally occurring substances can be used in their unaltered form. In addition, the retention and growth of the microorganism in the support are easy. An ordinary column can be advantageously used as the reaction vessel. Thus, this invention enables the microorganic reaction to be carried out economically and stably on a commercial scale.

Now, the present invention will be described more specifically with reference to working examples. It should be noted that the present invention is not limited to these examples.

*Nocardia erythropolis* KR-S-1 (referred to briefly as Nocardia and Pseudomonas KR-256-1 (referred to briefly as Pseudomonas) which appear in the specification have been deposited with Fermentation Research Institute, Agency of Industrial Science & Technology, Ministry of International Trade & Industry of Chiba City, Japan, on Apr. 19, 1976, assigned FERM P-No. 3530 and FERM P-No. 3529 respectively and are now available to the public. *Bacillus subtilis* (IAM 1521), *Penicillum chrysogenum* (IAM 7326) and *Staphylococcus aureus* (IAM 1011) are microorganisms, are in safekeeping at the Institute of Applied Microbiology, University of Tokyo, Tokyo, Japan and are also available to the public.

EXAMPLE 1

Soil of particles 0.15 to 0.8 mm in particle size and sea sand were mixed in a voluminal ratio of 1:2 and the resultant mixture was used as the support. A column 20 mm in inside diameter was packed with this support to a height of 100 mm. The amount of the support thus placed in the column was about 31.5 ml. The support thus held stationarily in the column was adjusted to pH 7 with a phosphate buffer. At room temperature, Nocardia was inoculated to the support at a proportion of $4 \times 10^8$ microorganism cells per gram of the support. The total number of the microorganism cells thus inoculated was about $1 \times 10^{11}$.

The support which now retained the microorganism cells was again adjusted to pH 7 with a phosphate buffer. Thereafter, an aqueous 3000-ppm (0.3%) di-2-ethylhexyl phthalate (DEHP) solution emulsified with a homogenate containing, as the nutritional source for the microorganism, 0.1% of ammonium sulfate, 0.02% of monobasic potassium phosphate, 0.16% of dibasic potassium phosphate, 0.02% of magnesium sulfate, 0.01% of calcium chloride, 0.01% of sodium chloride, 0.001% of iron sulfate, 0.0005% of sodium molybdate, 0.0005% of manganese sulfate, 0.0005% of sodium tungstate, 0.0004% of calcium pantothenate, 0.002% of inositole, 0.0004% of nicotin, 0.0002% of p-aminobenzoic acid, 0.0004% of pyridoxine hydrochloride, 0.0004% of thiamine hydrochloride, 0.0004% of riboflavin, 0.000002% of biotin and 0.0000005% of V-$B_{12}$ was agitated with a stirrer, blown amply with air and fed at room temperature to the column and allowed to flow down the column interior gravitationally. The feed rate of the solution was about 15 ml/hr and the retention time of the solution in the support was about two hours. From the effluent, samples were collected after lapse of 3, 7, 24, 48, 72 and 120 hours after start of the feeding of the solution to the column and the samples were tested for DEHP content.

For the purpose of comparison, the column was packed with the support having the same composition under the same conditions. With no microorganism inoculated to the support, the aqueous DEHP solution of the same composition was allowed to flow downwardly through the column gravitationally. The results were as shown in Table 2 below.

TABLE 2

| Time (hours) | 3 | 7 | 24 | 48 | 72 | 120 |
|---|---|---|---|---|---|---|
| Support retaining microorganism (ppm) | 50 | 0 | 0 | 0 | 0 | 0 |
| Support with no retained microoganism (ppm) | 1200 | 1290 | 1320 | 2600 | 1720 | 1500 |

It is evident from the table given above that the reaction substrate DEHP was substantially completely decomposed when the reaction substrate (aqueous solution containing 3% of DEHP) was passed through the support having the microorganism retained and cultivated therein, with absolutely no degradation of microorganic activity observed in the system without reference to the lapse of time.

The support used in the example described above was withdrawn from the column 32 days after completion of the experiment and was analyzed for residual DEHP content. It was confirmed consequently that the residual DEHP content was about 0.14% in the support retaining the microorganism and about 5.2% in the support retaining no microorganism, respectively based on the total DEHP supplied.

Immediately after the inoculation of microorganism cells and 32 days after completion of the experiment, one-gram samples of the support retaining the microoganism were examined to take count of the cells of Nocardia and all the cells including those of Nocardia. The results were as shown in Table 3. For this purpose was used in an ordinary bouillon agar medium.

TABLE 3

|  | Immediately after inoculation | After lapse of 32 days from end of experiment |
|---|---|---|
| Number of cells of Nocardia (/g) | $1 \times 10^{11}$ | $4 \times 10^{11}$ |
| Total number of cells | $1 \times 10^{12}$ | $1.45 \times 10^{12}$ |
| Ratio (Nocardia cells/total cells) | 10% | 28% |

It is evident from the foregoing table that Nocardia, on assimilation of DEHP, was retained and cultivated in the support, attained gradual propagation and effectively promoted the reaction.

The analysis of the samples for phthalate-ester content and that for residual phthalate-ester content were carried out as follows.

Analysis for phthalate-ester: This analysis for DEHP content was invariably carried out by gas chromatography (FID). Silicon OV-17 (2 m in length) was used as the column, with the column temperature fixed at 270° C. and the injection temperature at 300° C. $N_2$ gas was used as the carrier gas and a fixed amount of anthrone was added as the internal reference substance.

Analysis of residual phthalate-ester content: The total amount of the support (about 31.5 ml) was vigorously agitated with 100 ml of acetone and then left to stand at rest. A 50-ml portion of the resultant acetone phase was vigorously shaken with a mixed liquid consisting of 100 ml of water and 25 ml of n-hexane and then the n-hexane layer was removed. This procedure was performed twice and the resultant sample was analyzed by gas chromatography.

EXAMPLE 2

A support was formed by mixing soil, sea sand and sawdust in a voluminal ratio of 1:2:0.1. By following the procedure of Example 1 except using the support thus prepared, the same microorganism was inoculated to the support, the same aqueous solution of DEHP was passed through the column and the effluent was analyzed for DEHP concentration. For the purpose of comparison, the aqueous solution of DEHP was passed under the same conditions through the support of the same composition but retaining no microorganism and the eluate was subjected to the same analysis. The results were as shown in Table 4.

TABLE 4

| Time (hours) | 3 | 7 | 24 | 72 | 120 |
|---|---|---|---|---|---|
| Support retaining microorganism (ppm) | 39 | 0 | 0 | 0 | 0 |
| Support with no retained microorganism (ppm) | 1150 | 1650 | 1610 | 2700 | 1355 |

Similarly to Example 1, the support retaining the inoculated microorganism was withdrawn from the column 32 days after completion of the experiment. In a 1-gram sample of the support, count was taken of the number of cells of Nocardia and the total number of cells including those of Nocardia erythropolis. The results were as shown in Table 5.

TABLE 5

|  | Immediately after inoculation | After lapse of 32 days from end of experiment |
|---|---|---|
| Number of cells of Nocardia (/g) | $1 \times 10^{11}$ | $4 \times 10^{11}$ |

TABLE 5-continued

|  | Immediately after inoculation | After lapse of 32 days from end of experiment |
|---|---|---|
| Total number of cells | $1 \times 10^{12}$ | $1.5 \times 10^{12}$ |
| Ratio (Nocardia cells/total cells) | 10% | 27% |

Example 3

A support was formed by mixing soil and sea sand in a voluminal ratio of 1:2. A sludge obtained by inoculating Nocardia to activated sludge and acclimatizing the microorganism with DEHP for 14 days (Nocardia-acclimatized sludge), an activated sludge obtained by being acclimatized with DEHP for 14 days without inoculation of the microorganism (acclimatized sludge), and an activated sludge which had not been acclimatized at all (nonacclimatized sludge) were independently mixed homogeneously with the support in a fixed proportion of 1 g per 20 g of support. Each mixed support was placed stationarily in a column. The same aqueous solution of DEHP as used in Example 1 was allowed to flow downwardly through the column under the same conditions and the effluent was analyzed for DEHP concentration. For the purpose of comparison, the support in the form not mixed with any of the sludges was used and the feeding of the aqueous solution was carried out similarly, with the eluate analyzed for DEHP concentration. The results were as shown in Table 6.

The nutritional source which was used for the acclimatization contained 0.3% of DEHP, 0.12% of ammonium sulfate, 0.006% of magnesium sulfate, 0.06% of monobasic potassium phosphate and 0.48% of dibasic potassium phosphate.

TABLE 6

| Time (hours) | 3 | 7 | 24 | 48 | 72 | 100 |
|---|---|---|---|---|---|---|
| Nocardia-acclimatized sludge (ppm) | 0 | 0 | 0 | 0 | 0 | 0 |
| Acclimatized sludge (ppm) | 580 | — | 320 | 240 | 115 | 65 |
| Non-acclimatized sludge (ppm) | 1200 | — | 1250 | 2500 | 1600 | 600 |
| Support with no retained microorganism (ppm) | 1200 | — | 1320 | 2600 | 1720 | 1500 |

EXAMPLE 4

By following the procedure of Example 1, except using a support prepared by mixing Krilium (a soil conditioner consisting preponderantly of polyacrylic acid and made by Monsanto Chemical Co., U.S.A.) and sea sand in a voluminal ratio of 1:2, the aqueous DEHP solution was passed through the column. The effluent was analyzed for DEHP concentration. The results were as shown in Table 7.

TABLE 7

| Time (hours) | 24 | 72 | 120 |
|---|---|---|---|
| Support retaining microorganism (ppm) | 0 | 0 | 0 |
| Support with no retained microorganism (ppm) | 2500 | 3000 | 2900 |

From the column, the support retaining the inoculated microorganism was withdrawn 32 days after completion of the experiment. In a 1-gram sample of the support, count was taken of the number of cells of Nocardia. The number was $3 \times 10^{11}$, indicating that the microorganism propagated to about three times the number immediately after the inoculation.

EXAMPLE 5

To a support prepared by mixing soil and sea sand in a voluminal ratio of 1:2, Bacillus subtilis (IAM 1521) was inoculated in a proportion of 0.5 g as wet cells per 10 g of the support. A reaction solution (reaction substrate) having the same composition as that of Example 1, except using 0.2% of soluble starch instead of DEHP, was continuously fed to the column under the same conditions as those of Example 1.

From the effluent, samples were taken after lapse of 3, 24, 48 and 120 hours from the start of feeding of the reaction solution to the column and were analyzed for decomposition ratio of starch. The results were as shown in Table 8. The decomposition ratio of starch was determined by hydrolyzing the sample of effluent with hydrochloric acid and subjecting the hydrolyzate to Bertrand's reaction.

TABLE 8

| Time (hours) | Decomposition ratio of starch (%) | | | |
|---|---|---|---|---|
|  | 3 | 24 | 48 | 120 |
| Support retaining microorganism | 35 | 41 | 49 | 45 |
| Support with no retained microorganism | 12 | 8 | 5 | 9 |

It is evident from the foregoing table that the decomposition ratio of starch was notably high when the reaction was made with the support retaining the microorganism. The fairly high decomposition ratio of starch obtained in the initial stage of the reaction using the support not retaining the microorganism possibly suggests that starch particles were adsorbed or deposited on the soil particles and kept from flowing out of the support.

EXAMPLE 6

Soil was sterilized in an autoclave at 120° C. under one atmosphere and then air-dried under germfree. A support was prepared by mixing the dry soil with sea sand in a voluminal ratio of 1:3. A column 20 mm in inside diameter was packed with this support to a height of 100 mm. To the support was inoculated Penicillum chrysogenum (IAM 7326) which had been cultured in a medium consisting of 3 g of lactose, 1 g of glucose, 6 g of corn steep liquor, 0.3 g of $NaNO_3$, 0.05 g of $KH_2PO_4$, 0.012 g of $MgSO_4.7H_2O$ and 0.5 g of $CaCO_3$ for four days at 30° C. and consequently was obtained in the form of pellets.

Then to the column, an aqueous solution prepared by dissolving in 1 liter of distilled water the same amount of the mixture having the same composition as the medium described above and then adjusting the resultant solution to pH 5.5 was continuously fed at a feed rate of about 6 ml/hour.

After lapse of 24, 48 and 96 hours from the start of the feeding of said aqueous solution to the column, the effluent from the column was collected and analyzed for the production of penicillin of the inoculated microorganism. The results were as shown in Table 9.

TABLE 9

| Time (hours) | Immediately after inoculation | 24 | 48 | 96 |
|---|---|---|---|---|
| Activity (unit) | 1.2 | 2.5 | 3.8 | 7.5 |

The penicillin factor was determined by the cup method. The lower-layer medium in the dish was an aqueous solution prepared by dissolving 10 g of peptone, 5 g of beef extract, 2.5 g of NaCl and 15 g of agar in 1 liter of distilled water and then adjusting the resultant solution to pH 6.5 The upper-layer medium was an aqueous solution prepared by dissolving 10 g of peptone, 10 g of beef extract, 2.5 g of NaCl and 15 g of agar in 1 liter of distilled water and adjusting the resultant solution to pH 7. As the test microorganism which was most sensitive to the penicillin, there was used *Staphylococcus aureus* (IAM 1011).

EXAMPLE 7

Ordinary activated sludge resulting from cultivation in corn steep liquor was acclimatized with waste water containing petroleum including n-hexadecane (total organic carbon content of about 1,130 ppm) at about 30° C. for seven days, under continuous bubbling with air.

The acclimatized activated sludge obtained as described above was uniformly mixed with the support prepared under the same conditions as described in Example 1, and the resultant mixture was used to pack a column. The amount of the activated sludge thus added was about 10% by wet weight based on the support.

The same petroleum waste water as used in the aforementioned acclimatization was continuously fed to and allowed to flow down the aforementioned packed column gravitationally. The effluent from the column flowed down at a rate of about 15 ml/hr. This effluent was collected 4, 31 and 46 hours after start of the feeding of the waste water to the column, and the samples were tested for total organic carbon (TOC) content. For the purpose of comparison, the same petroleum waste water was treated under the same conditions as described above, except that the activated sludge used in the treatment had not undergone the acclimatization with the waste water. The effluent was similarly collected and the samples were tested for TOC content. The results were as shown in Table 10.

The test for TOC content was performed by using a TOC analyzer, Model 915, made by Beckman Corp. of the U.S.A.

TABLE 10

| Time (hours) | 4 | 31 | 46 |
|---|---|---|---|
| Acclimatized sludge (ppm) | 180 | 220 | 185 |
| Non-acclimatized sludge (ppm) | 790 | — | 990 |

After 31 hours' passage of the waste water through the packed column, a portion of the support in the column was collected and the sample was analyzed for microflora. The analysis showed that the microorganic cells of genera Nocardia and Pseudomonas had notably increased.

It is seen from the table that the preparatory acclimatization of the activated sludge with the reaction substrate brings about a remarkable effect.

Then, Nocardia and Pseudomonas which had been cultivated for seven days by using the aforementioned petroleum waste water as the culture medium were respectively added to ordinary activated sludge in the amount of about 10% by wet weight based on the activated sludge to prepare Nocardia-activated sludge and Pseudomonas-activated sludge.

The two activated sludges thus obtained were separately added in the amount of 10% by wet weight to the support prepared by the same procedure as described in the preceding example and uniformly mixed. The resultant mixtures were each used to pack a column. Subsequently, the petroleum waste water was continuously fed to and allowed to flow down the packed columns gravitationally. The effluents from the columns were collected 4, 22, 31, 46 hours after start of the feeding of waste water to the columns and the samples were tested for TOC content. The results were as shown in Table 11.

TABLE 11

| Time (hours) | 4 | 22 | 31 | 46 |
|---|---|---|---|---|
| Nocardia + sludge (ppm) | 90 | 55 | 79 | 37 |
| Pseudomonas + sludge (ppm) | 136 | 190 | 220 | 105 |

EXAMPLE 8

In a waste water containing 3,420 ppm of proteins (consisting of beef extract, peptone and NaCl in a proportion of 10:10:5) as TOC content, ordinary activated sludge was cultivated by way of acclimatization for seven days by following the procedure of Example 7.

The activated sludge thus acclimatized was mixed with the support under the same conditions as described in Example 7 and the resultant mixture was used to pack a column. The same protein-containing waste water as described above was continuously fed to and allowed to flow down the packed column gravitationally at room temperature. The effluent from the packed column was collected 4, 30 and 46 hours after start of the feeding of the waste water to the column and the samples were tested for TOC removal. For the purpose of comparison, the same protein-containing waste water was treated under the same conditions as described above, except that the activated sludge used in the treatment had not undergone the acclimatization with the waste water. The effluent from the column flowed down at a rate of about 12 ml/hour. The results were as shown in Table 12.

TABLE 12

| Time (hours) | 4 | 30 | 46 |
|---|---|---|---|
| Acclimatized sludge (%) | 70 | 72 | 75 |
| Non-acclimatized sludge (%) | 24 | 13 | 23 |

After 30 hours' passage of the waste water through the packed column, a portion of the support in the column was collected and the sample was analyzed for microflora. The analysis showed that the microorganic cells of genus Pseudomonas had notably propagated.

Then, by following the procedure of Example 7, Nocardia and Pseudomonas which had been cultivated by using the protein-containing waste water as the culture medium were respectively added to ordinary activated sludge in the amount of about 10% by wet weight based on the activated sludge to prepare Nocardia-activated sludge and Pseudomonas-activated sludge. The two sludges were separately added to the support each in the amount of 10% by wet weight. The resultant mixtures were each used to pack a column.

The same protein-containing waste water as used in the aforementioned acclimatization was continuously fed to and allowed to flow down the packed columns gravitationally. The effluents from the packed columns were collected 4, 22, 30 and 46 hours after start of the feeding of the waste water to the packed columns and the samples were analyzed for TOC removal. The results were as shown in Table 13.

TABLE 13

| Time (hours) | 4 | 22 | 30 | 46 |
|---|---|---|---|---|
| Nocardia + sludge (%) | 72 | 85 | 77 | 75 |
| Pseudomonas + sludge (%) | 82 | 80 | 79 | 85 |

EXAMPLE 9

The procedure of Example 7 was followed, except that the petroleum waste water was replaced by a synthetic waste water having 6 g of glucose, 1 g of peptone and 1 g of $KH_2PO_4$ dissolved in 1 liter of water (TOC content 3,665 ppm).

The effluent which gravitationally flowed out of the column was collected 5, 24, 48 and 72 hours after start of the feeding of the synthetic waste water and the samples were analyzed for TOC removal. The results were as shown in Table 14.

TABLE 14

| Time (hours) | 5 | 24 | 48 | 72 |
|---|---|---|---|---|
| Acclimatized sludge (%) | 88 | 57 | 70 | 72 |
| Non-acclimatized sludge (%) | 33 | 18 | 12 | 11 |

Nocardia and Pseudomonas which had been cultivated with the same synthetic waste water by way of acclimatization were respectively added to ordinary activated sludge and mixed with the support to prepare Nocardia-activated sludge and Pseudomonas-activated sludge. The synthetic waste water was treated by using the two sludges. The results were as shown in Table 15.

TABLE 15

| Time (hours) | 5 | 24 | 72 |
|---|---|---|---|
| Nocardia + sludge (%) | 78 | 64 | 70 |
| Pseudomonas + sludge (%) | 61 | 66 | 65 |

EXAMPLE 10

The procedure of Example 7 was followed, except that the petroleum waste water was replaced by a carbohydrate waste water containing soluble starch, peptone and $KH_2PO_4$ at a proportion of 3:1:1 and having a TOC content of 1,950 ppm.

The effluent which gravitationally flowed out of the column was collected 3, 24 and 48 hours after start of the feeding of the waste water to the packed column and the samples were analyzed for TOC removal. The flow rate of the effluent from the column was about 10 ml/hour. The results were as shown in Table 16.

TABLE 16

| Time (hours) | 3 | 24 | 48 |
|---|---|---|---|
| Acclimatized sludge (%) | 71 | 73 | 70 |
| Non-acclimatized sludge (%) | 8 | 8 | 5 |

After 24 hours' treatment, a portion of the support in the column was removed and the sample was analyzed for microflora. The analysis showed that the microorganic cells of genus Bacillus were notably increased.

Then, *Bacillus subtilis* (IAM 1521) was precultivated for seven days in the aforementioned carbohydrate waste water and mixed with ordinary activated sludge. The resultant mixture was carried on the support and then used to pack a column. The carbohydrate waste water was treated by passage through this packed column. The effluent from the packed column was collected 3, 24 and 48 hours after start of the feeding of the waste water to the packed column. The samples were analyzed for TOC content. The results were about 51, 45 and 55% respectively.

What is claimed is:

1. A method of conducting a biochemical reaction to dispose of a phthalate ester with a microorganism comprising:
    filling a vessel capable of passing liquids therethrough with a hydrophilic support thereby forming a packed bed of said support having a pH in the range from 3 to 9 and which has the capability of retaining and promoting the cultivation of a microorganism;
    inoculating said support with *Nocardia erythropolis*;
    passing an aqueous dispersion of a phthalate ester through said vessel thereby permitting said *Nocardia erythropolis* to react with the phthalate ester as it passes through the packed bed; and
    maintaining the growth of the *Nocardia erythropolis* as it continues to react with the passing phthalate ester.

2. The method according to claim 1 wherein said microorganism is inoculated on said support in the form of an acclimatized activated sludge.

3. The method according to claim 1, wherein said hydrophilic support is soil.

* * * * *